United States Patent
Claus et al.

(10) Patent No.: US 6,888,924 B2
(45) Date of Patent: May 3, 2005

(54) METHOD, APPARATUS, AND MEDIUM FOR CALIBRATION OF TOMOSYNTHESIS SYSTEM GEOMETRY USING FIDUCIAL MARKERS WITH NON-DETERMINED POSITION

(75) Inventors: Bernhard Erich Hermann Claus, Niskayuna, NY (US); Beale Opsahl-Ong, Darien, CT (US); Mehmet Yavuz, Plano, TX (US)

(73) Assignee: General Electric Company, Niskayuna, NY (US)

( * ) Notice: Subject to any disclaimer, the term of this patent is extended or adjusted under 35 U.S.C. 154(b) by 135 days.

(21) Appl. No.: 10/607,554

(22) Filed: Jun. 25, 2003

(65) Prior Publication Data

US 2004/0264648 A1 Dec. 30, 2004

(51) Int. Cl.[7] ................................................. H05G 1/28
(52) U.S. Cl. ........................ 378/163; 378/205; 378/207
(58) Field of Search .............................. 378/21, 23, 62, 378/162, 163, 164, 205, 207, 901; 382/128, 131

(56) References Cited

U.S. PATENT DOCUMENTS

| | | | |
|---|---|---|---|
| 5,872,828 A | 2/1999 | Niklason et al. | 378/23 |
| 6,196,715 B1 | 3/2001 | Nambu et al. | 378/197 |
| 6,671,349 B1 * | 12/2003 | Griffith | 378/163 |

* cited by examiner

Primary Examiner—Edward J. Glick
Assistant Examiner—Courtney Thomas
(74) Attorney, Agent, or Firm—Jean K. Testa; Christian G. Cabou (57) ABSTRACT

Geometry of a tomosynthesis system including a detector and an x-ray source is determined using fiducial markers with non-determined positions. The geometry is determined by arbitrarily identifying at least two markers within an imaged volume, at different relative distances between the detector and the x-ray source, without having projections located on a straight line for all different source positions, and locating the projections of the markers within at least two images acquired of the imaged volume. The at least two images correspond to different positions of a focal spot of the x-ray source.

39 Claims, 5 Drawing Sheets

METHOD, APPARATUS, AND MEDIUM FOR CALIBRATION OF TOMOSYNTHESIS SYSTEM GEOMETRY USING FIDUCIAL MARKERS WITH NON-DETERMINED POSITION

BACKGROUND OF THE INVENTION

In a typical tomosynthesis system, an x-ray source emits x-ray beams in the direction of an object to be imaged. These x-ray beams are subsequently detected by a detector, and are acquired by the tomosynthesis system.

Further, in a typical tomosynthesis system, the imaged object remains in a fixed position, the x-ray source assumes different discrete positions along a trajectory in space. For each source position, a projection radiograph image is acquired.

Once the images, included in the detected x-ray beams, of the object are acquired by the tomosynthesis system, reconstruction of three-dimensional structures of the imaged object from structures included in the acquired images is accomplished by the tomosynthesis system. Accurate and reliable reconstruction of 3-dimensional information about structures of the imaged object in tomosynthesis requires a precise knowledge of the tomosynthesis system geometry. The relative positions of the focal spots of the x-ray source for the different x-ray source locations, and the detector at the time the images of the object are being acquired is referred to as the tomosynthesis system geometry. The focal spot is the location of the point-like approximation of the x-ray source. The focal spot is typically at a fixed location with respect to the elements of the x-ray source. For the purposes of reconstruction, the focal spot represents the location of the x-ray source. This precise knowledge of the tomosynthesis system geometry is required in order to obtain a high image quality and a high level of detail-resolution of reconstructed structures in the imaged, 3-dimensional object.

One conventional method of determining the tomosynthesis system geometry is by physically measuring the spatial location and orientation of the different components (the detector and the focal spot positions of the x-ray source at the different source locations). This method requires a number of precise measurements different source locations). This method requires a number of precise measurements and is typically complex, depending on the mechanical structure which connects the detector and the x-ray source.

Moreover, other conventional methods can be used that are similar to calibrating an internal camera geometry using images of scenes with unknown geometry. Although conceptually similar to the problem of determining the tomosynthesis system geometry from images of some object, these other conventional methods cannot be carried over to determining tomosynthesis system geometry because a tomosynthesis system includes a different system geometry for each acquired image, typically because of a change in the x-ray source (and thus focal spot) location for each acquired image.

In computed tomography (CT), there exist approaches that employ markers (or phantoms) with a well-defined relative position of the markers. However, these approaches are based upon the use of a well-defined phantom (which is relatively expensive), and usually cannot be used while imaging a patient. Consequently, the imaging procedure has to be repeated if the CT system geometry was not well calibrated during the patient image acquisition.

BRIEF SUMMARY OF THE INVENTION

Geometry of a tomosynthesis system including a detector and an x-ray source is determined in the present invention using fiducial markers with non-determined positions. The geometry is determined by arbitrarily locating at least two markers within the imaged volume, at different relative distances between the detector and the x-ray source, without having projections located on a straight line for all different source positions, and locating the projections of the markers within at least two images acquired of the imaged volume. The at least two images correspond to different positions of a focal spot of the x-ray source, and for every x-ray source position one acquired image must be included in the at least two images.

Further, the present invention determines and analyzes the focal spot positions for images. That is, if two images are analyzed by the present invention, then the corresponding two focal spot locations are determined for those images even when more images for different focal spot positions have been acquired.

In addition, the present invention uses a phantom including fiducial markers to determine tomosynthesis system geometry. The used phantom does not need to be a rigid structure, but it can comprise fiducial markers which are physically separate from each other and that remain stationary during the image acquisition process. Use of a non-rigid structure as the phantom (or even separate markers, that are not mechanically connected with each other) allows for simultaneous imaging of an object.

More particularly, in the present invention, a set of projection images is acquired by a tomosynthesis system, and the position of the focal spot of the x-ray source (relative to the detector) for at least two of the projection images, as well as the location of the markers (relative to the detector), is determined from the position of the shadows (i.e., the projections) of the fiducial markers. In particular, no well-defined phantom is required, but a phantom comprising a non-rigid arrangement of markers that satisfies a general condition is used. In the present invention, at least two markers are identified in an imaged volume (which may include the imaged object at the same time). These two markers (discussed herein below as markers B, B') are identified consistent with the following criteria. These two markers are placed in the imaged volume at different heights relative to the detector. Moreover, these two markers are placed in the imaged volume such that the plurality of projection images (or shadows) of the two markers, for all x-ray source positions, is not located on a straight line.

Quality of reconstruction images in which back-projections of projections of any single point (within the imaged volume) line up in space is optimal and is in particular enhanced over that of reconstruction images in which the back-projections do not line up in space. Thus, in the present invention, the tomosynthesis system geometry is extracted from the images by fitting the tomosynthesis system geometry to the position of the projections of suitable features in the images.

Thus, in the present invention, the location of the images of a set of fiducial markers is identified in each of the acquired projection images, and the correspondences between projection images (shadows) and markers are determined. From this identification, the geometry of the tomosynthesis system (i.e., the relative position of the focal spot of the x-ray source for at least two of the x-ray source positions with respect to the detector) as well as the location of the fiducial markers is determined.

Further, the present invention comprises a method determining the geometry of a tomosynthesis system (i.e., system geometry calibration) by using the projection images of a phantom containing fiducial markers with unknown position.

More particularly, the present invention uses a phantom with an almost arbitrary arrangement of fiducial markers, and does not require a special phantom with well-defined relative positions of the markers. Projection radiograph images of this phantom are acquired, and the positions of the projections of the markers in the images are assumed to be known (i.e., measurements of the locations of the shadows of the markers are assumed to be available). From this data set, a set of estimated focal spot locations as well as the associated estimated locations of the markers are derived such that optimal quality of the reconstructed images is guaranteed.

The present invention comprises, at least, a method, a tomosynthesis system, and a computer-readable medium storing a program that when executed by a computer causes the computer to execute processes, comprising determining geometry of a tomosynthesis system including a detector and an x-ray source. The method and tomosynthesis system comprise and/or execute steps including arbitrarily identifying at least two markers within an imaged volume, at different relative distances between the detector and the x-ray source, and without having projections located on a straight line for all different source positions. A computer is also used to locate the projections of the markers within at least two images acquired of the imaged volume. The at least two images correspond to different positions of a focal spot of the x-ray source.

The present invention also comprises a computer-readable medium that stores a program for determining geometry of a tomosynthesis system that includes, at least, a detector, an x-ray source and at least two markers arbitrarily placed within an imaged volume, at different relative distances between the detector and the x-ray source, and without having projections located on a straight line for all different source positions. The program which when executed by a computer causes the computer to execute the processes including the steps of locating by the computer of the tomosynthesis system the projections of the markers within at least two images acquired of the imaged volume. The at least two images correspond to different positions of a focal spot of the x-ray source.

DETAILED DESCRIPTION OF THE INVENTION

As used herein, the terms "adapted to", "configured to" and the like refer to the components that are arranged to provide a desired function as might be know to one skilled in the art. For example, in the situation of the processing of signals, data and the like, the term "adapted to" refers to a component such as, for example, a preprogrammed digital computer, an application-specific integrated circuit (ASIC), or other electronic, analog or optical computing device that can be prepared to process input signals in accordance with a desired algorithm to provide a desired output signal. In the situation of a mechanical or electromechanical device, the term "adapted to" refers to the components, for example, being assembled, connected or disposed in an operational relationship so as to provide a desired functionality, make up or arrangement in a device.

Throughout the description of the present invention, reference is made to the x-ray source being "above the detector", or a "constant height above the detector". This reference is made for clarity of explanation, and means that the x-ray source is positioned opposite to the detector relative to the imaged object and merely explains the relative positions of the x-ray source and the detector (or detector plane). Reference to the x-ray source being "above the detector" does not imply that the x-ray source is necessarily positioned "higher than the detector" since the present invention can be implemented successfully, for example, if the digital tomosynthesis system is turned upside down, so long as the relative geometry of the digital tomosynthesis system remains unchanged.

Figure 1:
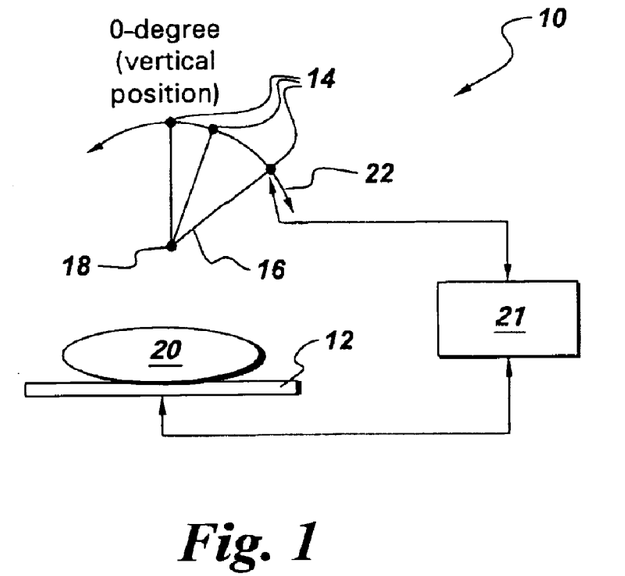
FIG. 1 shows an exemplary embodiment of a system geometry of a tomosynthesis system.

The present invention is described with reference to the tomosynthesis system 10 shown in FIG. 1. In the tomosynthesis system 10 shown in FIG. 1, a tomosynthesis system for breast imaging, the detector 12, for example, can be horizontal and stationary, while the x-ray source 14 is attached to a gantry arm 16 which rotates around a pivot point 18 in order to acquire the projections from different view angles of an object 20. The pivot point 18 is located at some fixed distance above the detector 12 (for example, about 22.4 cm.), and the distance from focal spot of the x-ray source 14 to the pivot point 18 is also fixed (for example, about 44.0 cm.). The considered angular range of the gantry 16 (with respect to the pivot point 18) is from about −25 to 25 degrees, where 0 degrees corresponds to the vertical position of the gantry arm. That is, x-ray source 14 travels along a trajectory 22 as shown in FIG. 1. Moreover, the detector 12 is provided in a detector plane (not shown in FIG. 1). It should be appreciated in other embodiments that the detector 12 can also move with relation to the x-ray source 14 and/or the object 20.

In addition, the tomosynthesis system 10 shown in FIG. 1 comprises computer 21. Computer 21 is coupled to detector 12 and to x-ray source 14. Computer 21 controls the movement of the x-ray source 14 and/or the detector 12, as well as the timing of the exposure by the x-ray source 14 and the readout of the detector 12. The computer also determines the geometry of the tomosynthesis system 10 from the acquired projection images according to the method of the present invention discussed herein below. That is, computer 21 comprises software executed by the computer 21, which determines the geometry of the tomosynthesis system 10 in accordance with the method discussed herein. It should be appreciated that the computer 21 can comprise various types of computing devices, for example, without limitation, a microprocessor, a digital computer and a server.

The tomosynthesis system 10 shown in FIG. 1 is exemplary, and the present invention is not constrained to the geometry of the tomosynthesis system 10 shown in FIG. 1.

In the ensuing discussion, reference is made generally to the position of the focal spot location of the x-ray source (or tube) 14. The orientation of the x-ray source (or tube) 14 can be modified through rotation without changing the focal spot position, and the orientation of the x-ray source 14 will be adjusted typically such that the center of the x-ray beam emitted by the x-ray source 14 is close to the center of the detector 12.

The focal spot is the location of the point-like approximation of the x-ray source 14. The focal spot is generally at a fixed location with respect to the elements of the x-ray source 14. That is, the focal spot represents the location of the x-ray source 14.

The markers, which are not shown in FIG. 1, may be contained in a rigid phantom, but may also be arranged separately. In one embodiment, the markers can be arranged:

such that at least two markers have different heights above the detector 12, and such that the set of projection images of these two markers (for projection radiographs taken at different focal spot positions of the x-ray source 14) do not lie on a single line in the detector plane.

To compensate for errors in the measurement of the locations of the markers' projections, it is desirable to have several markers such that a maximum number of pairs of markers can be formed which satisfy the above-mentioned conditions.

Determination (or reconstruction) of the tomosynthesis system geometry in accordance with the present invention is now disclosed. Reconstructing tomosynthesis system geometry means "to make everything line up", as explained. The (estimated) geometry of the tomosynthesis system is "perfect" from an image quality standpoint, only if "everything lines up perfectly in the backprojection". That is, if for every point in space, the lines between the different (reconstructed) focal spot positions of the x-ray source 14 and the corresponding projections of the considered point (with respect to the "true", but unknown, focal spot positions) intersect at a single point (the "backprojected" point). In terms of image quality, it is irrelevant whether the original point and the backprojected point do in fact coincide or not. Note that image quality, as it is referred to here, only takes into account effects due to a relative misalignment or inconsistency of the assumed system geometry. In that sense, a reconstruction of the relative system geometry (referred to herein below) relates to a tomosynthesis system geometry that is, given only geometric relations within the projection images, undistinguishable from the true and absolute tomosynthesis system geometry.

Since "everything lines up in the backprojection" in the present invention, reconstruction of the imaged object can be performed using any 3-dimensional reconstruction algorithm known in the art and should not be interpreted as being restricted to using a 3-dimensional reconstruction algorithm of the back-projection type.

Moreover, if precise 3-dimensional reconstruction of the structures in the imaged object in absolute coordinates is not required, then the present invention obtains an estimate of the relative system geometry leading to an optimal image quality of the reconstruction (i.e., without any blurring or other artifacts caused by errors in the assumed system geometry) without determining uniquely the absolute system geometry from the projection images. A derivation of obtaining an estimate of both, the relative and the absolute tomosynthesis system geometry leading to an optimal image quality of the reconstruction is presented in further detail herein below. The tomosynthesis system geometry (or an equivalent tomosynthesis system geometry) is determined precisely in order to obtain optimal image quality for the reconstruction of the imaged object.

A discussion of the Desargues' theorem and how Desargues' theorem connects the different components of the tomosynthesis system geometry is presented herein below. Desargues' theorem states that if the lines joining corresponding vertices of two triangles pass through a common point, then the points of intersection of corresponding sides lie on a straight line. The corresponding dual theorem states that if the corresponding sides of two triangles have points of intersection that lie on a straight line, then the lines joining corresponding vertices pass through a common point. An example 30 of Desargues' Theorem is illustrated in FIG. 2, where the triplets of points (A,B,C) and (A',B',C'), respectively, describe the two triangles referred to in Desargues' theorem (or the dual theorem).

Figure 2:
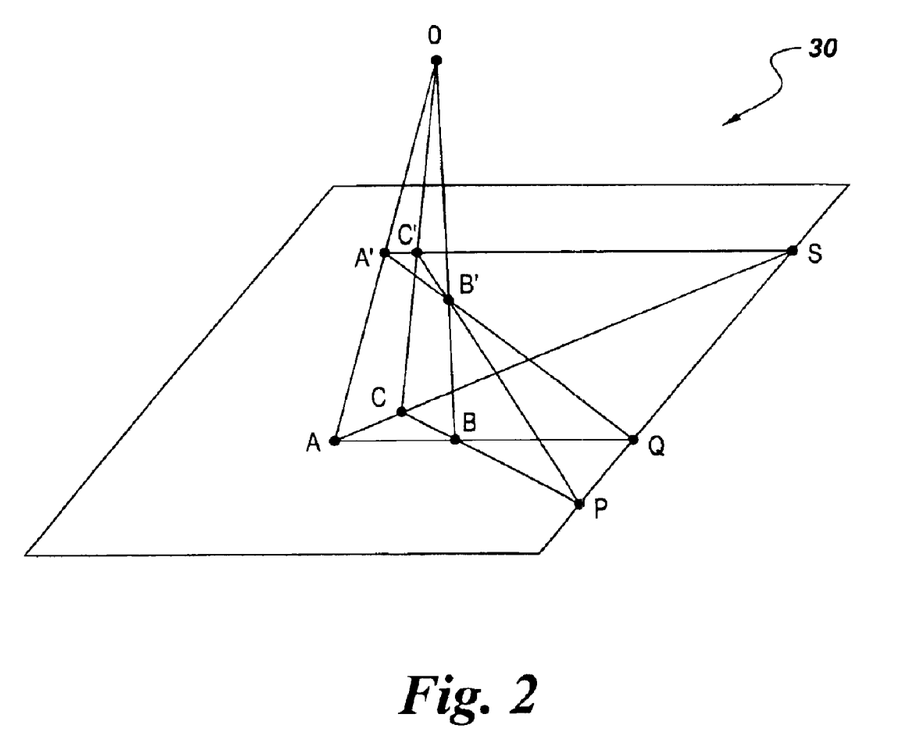
FIG. 2 shows an example illustrating Desargues' Theorem.
Figure 3:
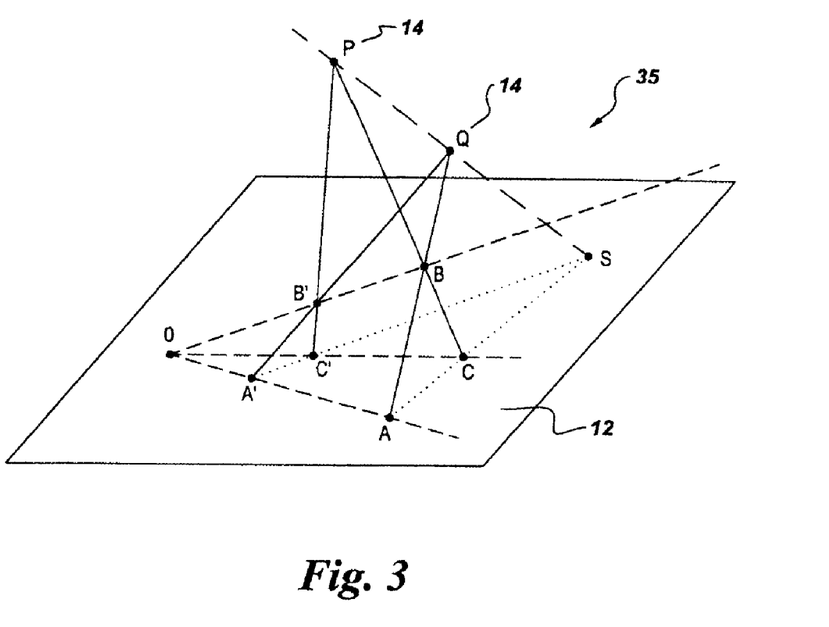
FIG. 3 is a diagram illustrating the relation between Desargues' Theorem illustrated in FIG. 2 to the tomosynthesis system shown in FIG. 1.

FIG. 2 shows an example 30 illustrating Desargues' theorem, and FIG. 3 is a diagram 35 relating Desargues' Theorem 30 shown in FIG. 2 to the tomosynthesis system 10 shown in FIG. 1. That is, FIG. 3 shows the relation 35 between the tomosynthesis system 10 and Desargues' theorem.

FIGS. 2 and 3 are discussed together. In both FIGS. 2 and 3 the marked points are identified as follows:

P and Q denote two different focal spot positions of the X-ray source 14,

B and B' denote two different fiducial marker positions,

A and A', C and C' denote the respective locations of the projections of the markers B and B', generated by acquiring projection images with the focal spot positions of the x-ray source being located at points Q and P.

Therefore, the points A, C, A', C', O and S all lie in the detector plane corresponding to, for example, detector 12 of FIG. 1.

In the example 35 of FIG. 3 (and the example 30 of FIG. 2), the points A, C and A', C' are the shadows of the markers B, B' (of unknown position), with respect to the (unknown) focal spot positions P and Q. These observed points do, however, uniquely define the points O and S, as explained in detail herein below. FIG. 3 (in which the points P and Q denote two different focal spot positions and B, B' denote the position of the two fiducial markers) illustrates the conditions satisfied by the used fiducial markers. The condition that the two markers have different heights above the detector 12 translates into the fact that point O, where the line through B and B' intersects the detector plane, is well-defined. Further, the condition that the set of projection images of these two markers (for different focal spot positions) do not lie on a single line in the detector plane 12 translates into the fact that the lines through A', A, and C', C, respectively, are two separate lines which intersect at the point O (and not a single line which passes also through the point O).

With the method of the present invention, estimates of the position of the focal spot positions P and Q (as well as any additional focal spot positions) and corresponding estimates of the location of the fiducial markers B and B' (and any other, additional markers) are determined from the observed projections.

Figure 4:
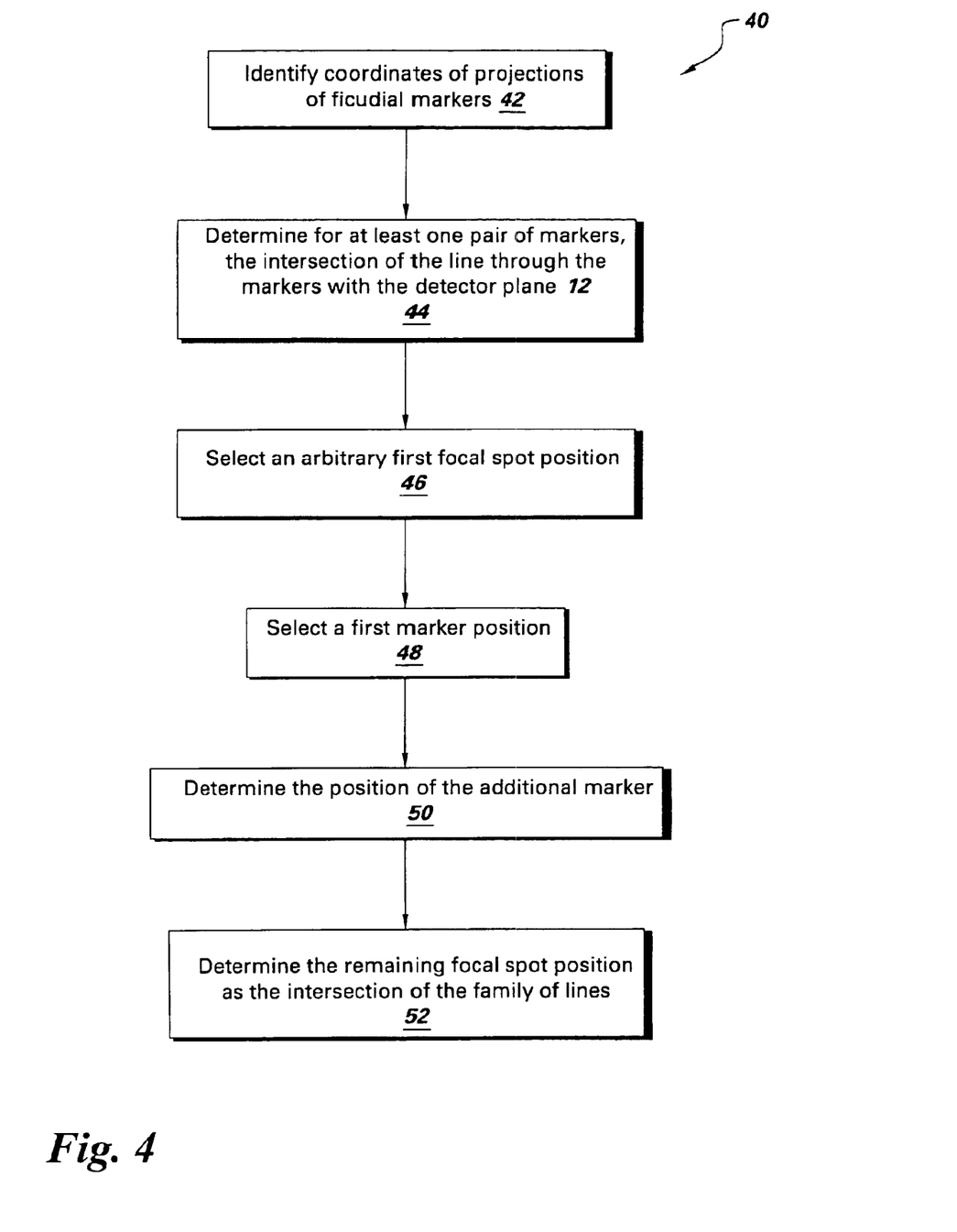
FIG. 4 shows a method of reconstructing tomosynthesis system geometry of the present invention.

FIG. 4 shows a method 40 of reconstructing tomosynthesis system geometry using the present invention. The method 40 shown in FIG. 4 is discussed with respect to the relation 35 shown in FIG. 3, and is implemented by computer 21 shown in FIG. 1. Computer 21 can comprise a computer-readable medium on which a program is stored which when executed by computer 21 causes computer 21 to execute the processes corresponding to the following method of the present invention.

As shown in FIG. 4, the method 40 comprises identifying coordinates of the projections (or shadows) of the fiducial markers, including identifying for each point the index of the associated markers as well as the index of the associated focal spot position of the x-ray source 14 (step 42). It should be appreciated that these projections (or shadows) of the markers can be located either automatically, or manually by an operator of the system. The markers are, for example, spherical radiologically opaque objects. Then their shadows are ellipses, and the centers of these ellipses are good approximations for the location of the shadow of the center of the spherical objects. Markers B, B', for example, include high-contrast, spherical materials such as steel or lead spheres (or BBs) as discussed herein above, or crosshairs of wires, or other suitable structures. The markers are arranged to satisfy the above-mentioned conditions and such that it is easy to identify which shadow (i.e., projection image of a marker) corresponds to which marker. In addition, the fiducial makers can comprise anatomical markers, such as, for example, bones, organs and/or other anatomical objects. An index of the focal spot position of the x-ray source 14 is, essentially, an index of the considered projection image; all markers are assumed to have projections within each image.

Alternatively, the present invention can be easily modified such that a reconstruction of the tomosynthesis geometry is possible even if only shadows of a subset of the markers is visible in each of the acquired images (due to the fact that the shadows of some markers may not fall onto the detector 12 for every focal spot position of the x-ray source 14). In this case, however, for each projection image, there must be another projection image acquired for a different focal spot position of the x-ray source 14, such that at least two of the markers have shadows in both images, and any two projection images must be connected by a chain consisting of these relationships between projection images.

Next, the method 40 of the present invention determines for at least one pair of markers B, B' the intersection O of the line through B, B' with the detector plane 12 (step 44). This point is given as the intersection of a family of lines, where each line goes through the projections of both B and B' for a single focal spot position. In FIG. 3 these lines are (1) the line through A and A' (projections of B and B' corresponding to focal spot position Q), and (2) the line through C and C' (projections corresponding to focal spot position P). Next, the method 40 selects an arbitrary first focal spot position P (at some "reasonable" location above the detector 12) (step 46).

Then, the method 40 selects the first marker position B as an arbitrary point between P and the corresponding projection C, located on the line through P and C (step 48). An example of selection 48 is if P and C are given by $$P = \begin{pmatrix} x_P \\ y_P \\ z_P \end{pmatrix} \text{ and } C = \begin{pmatrix} x_C \\ y_C \\ z_C \end{pmatrix},$$

respectively, then the point B is given by $$B = \begin{pmatrix} x_B \\ y_B \\ z_B \end{pmatrix} = \lambda \cdot \begin{pmatrix} x_P \\ y_P \\ z_P \end{pmatrix} + (1-\lambda) \cdot \begin{pmatrix} x_C \\ y_C \\ z_C \end{pmatrix}$$

for some λ between zero and one.

Subsequently, the method 40 determines the location of the additional marker B' as the intersection of the line through B and O with the line through the focal spot P and the corresponding projection C' of B' (step 50). If more additional markers are considered, the method 40 determines 50 their respective location in a similar manner.

Then, the method 40 determines the remaining focal spot position Q as the intersection of the family of lines, each passing through an estimated marker position B (or B') and the corresponding projection A (or A') (step 52). The method 40 takes into account the corresponding lines associated with any additional markers that may be present. The method 40 also determines 52 the locations of any additional focal spot positions in a similar manner.

Using the method 40 of FIG. 4, a consistent set of focal spot and fiducial marker positions for the tomosynthesis system 10 is determined.

In any one of steps 44, 50, and 52, respectively, of the method 40, a larger number of points/markers can be used than is presented here. These additional points/markers can lead to an increased robustness of the present invention with respect to measurement errors that may have occurred during step 42, but will typically involve estimating the optimal position of the respective points to be determined. That is, usually the involved lines may not intersect at a single point, in which case, for example, a least squares technique can be used to estimate an optimal intersection point.

Figure 5:
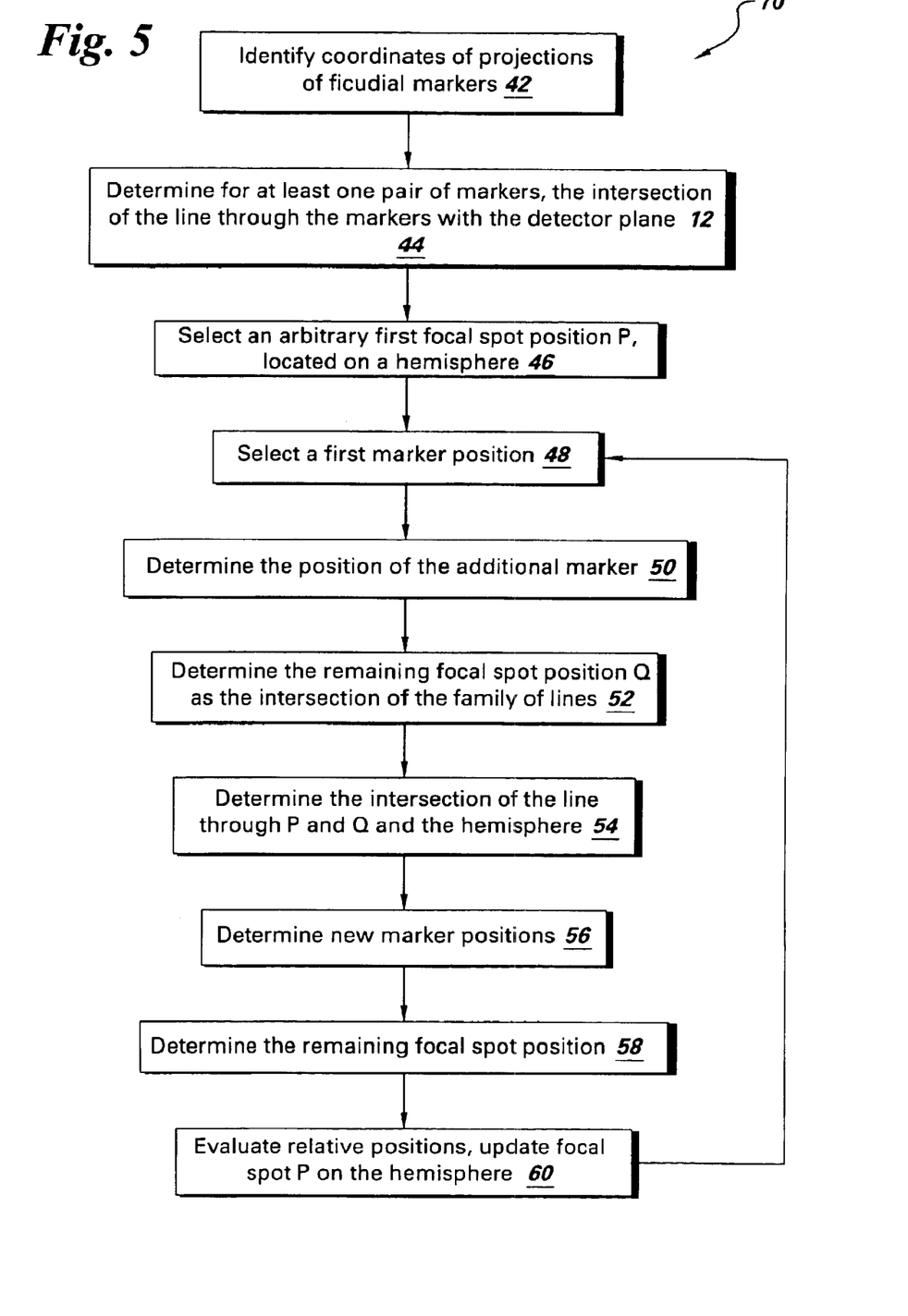
FIG. 5 is an example flowchart of iterative geometry reconstruction method of the present invention.

An example of a method to determine an optimal estimate of a point of intersection between two (or more lines), corresponding to steps 44, 50, and 52 in method 40 (and same in method 70 (FIG. 5), discussed herein below) is presented. The following method is applicable to lines in planes, in 3-dimensional space, and higher-dimensional spaces. More particularly, if a line with index i is determined by the points $u_i$ and $w_i$ (both points being located on the line), where $u_i$ and $w_i$ are column vectors containing the coordinates of the points, and $v_i$ is defined to be the normalized orientation vector of that line. In particular, the vector $v_i$ is computed as the difference of $u_i$ and $w_i$, i.e., $v_i = u_i - w_i$ with a subsequent scaling (i.e., multiplication with a constant factor) such that it is a vector of length one. Using this notation, the optimal point of intersection x is determined by solving the following 3×3 (corresponding to lines in three dimensional space) system of linear equations, $$\left[ N \cdot Id - \sum_{i=1}^{N} v_i v_i^T \right] \cdot x = \sum_{i=1}^{N} (u_i - (u_i^T v_i) \cdot v_i),$$

where Id denotes the 3×3 identity matrix, and N is the number of considered lines. For lower dimensional spaces (i.e., planes) or higher dimensional spaces, the dimensions of the system of linear equations, and the involved identity matrix, are adjusted accordingly. The obtained result (i.e., the resulting point x) is optimal in the sense that the obtained result minimizes the sum of squared distances from the resulting point x to the respective lines. If the lines do in fact intersect in a single point, then this approach yields this point as the result (note that in three dimensions, unlike in the plane, different lines do not necessarily intersect, even if they are not parallel). Alternative approaches to determining an estimate of the point of intersection between several lines may be used as well.

As will become clear from the derivation of the method 40 presented herein below, the method 40 can be modified. One such modification involves, for example, starting by determining the point S from the data as the intersection of lines through the points A', C' and A, C, respectively. Then selecting an arbitrary first focal spot position P, choosing a second focal spot position Q at some arbitrary location on the line through P and S, and then determining any marker position B (or B', . . . ) as the intersection of the lines through the focal spot positions P (and Q) and the corresponding projections of the considered marker. From these reconstructed elements all remaining focal spot positions are readily determined by proceeding according to step 52 of method 40 presented herein above.

In the tomosynthesis system 10 shown in FIG. 1, however, the line through any pair of focal spot (or x-ray source 14) positions P, Q intersects the detector plane 12 at a relatively large distance from the used phantom (B, B') and the corresponding projections A, C, A' and C'. This is a consequence of the variation in height between focal spot positions P, Q being relatively small, which leads to an increased sensitivity to measurement errors when determining the point S. For other system geometries (which differ from the tomosynthesis system 10 of FIG. 1), the focal spot positions P, Q may be arranged at a constant height above the detector 12. Consequently the point S, which is defined to be the intersection of the line through the points P and Q with the detector plane, is not uniquely defined, which prohibits the use of the modified approach as outlined herein above.

On the other hand, the location of markers B, B' in the phantom can be roughly arranged such that for some pairs of markers B, B' the intersection of the line through these markers B, B' with the detector plane 12 (i.e., the location of the point O) is relatively close to the projection of these markers B, B' onto the detector plane 12. In this case, the computation of the location of the point O is robust with respect to measurement errors, even when the focal spot positions P, Q are all at a constant height above the detector 12. Therefore, method 40 of FIG. 4 is the preferred embodiment of the present invention used to determine the tomosynthesis system geometry.

The above-mentioned method 40 obtains the relative geometry of the tomosynthesis system. Relative geometry means that the image quality is optimal and that there is no loss in image quality due to unknown perturbations of the tomosynthesis system geometry. The relative geometry may not be the absolute (i.e., the "true") geometry of the tomosynthesis system.

Reconstruction of the absolute geometry of the tomosynthesis system 10 is now discussed. The absolute geometry of the tomosynthesis system means an absolute geometry of the tomosynthesis system with respect to a fixed coordinate system within the tomosynthesis system. The fixed coordinate system typically includes the detector 12 as a reference point.

The method 40 leads to a system geometry with perfect "image quality" (as discussed earlier), but may be far from the "true" system geometry. To obtain a system geometry which is closer to the true geometry (or even coincides with the true geometry), additional constraints need to be introduced. As an example of additional constraints, point P is selected to be the "true" focal spot location (which may be considered to be a particularly reliable estimate, due to specific characteristics of the mechanical system), and one additional parameter is chosen, such as the height of the marker B above the detector plane 12. Other constraints may include for example the known distance between markers, the size of markers, the known distance between focal spots, etc. Presented herein below is a method for the reconstruction of the absolute tomosynthesis system geometry, which is specifically adapted to the tomosynthesis system geometry 10 of FIG. 1 in that the used additional constraint takes into account that the x-ray source traverses a trajectory which is located at a fixed distance from a pivot point, i.e., the focal spot positions are located on a hemisphere. This approach can be easily modified, using other additional constraints as the ones presented herein above, to accommodate other tomosynthesis system geometries.

To reconstruct the absolute tomosynthesis system geometry, method 40 is integrated into an iterative geometry reconstruction method 70 (FIG. 5). In the iterative geometry reconstruction method 70 (applied specifically with respect to the tomosynthesis system geometry 10 of FIG. 1), the distance of the computed focal spot locations P,Q from a hemisphere is minimized. The location of the focal spot positions on a hemisphere is used here to reconstruct the absolute system geometry. The radius of the hemisphere is determined by an assumed length of the gantry arm 16. The center of the hemisphere is given by the corresponding pivot point 18 shown in FIG. 1. In particular, step 46 of method 40 is modified to select P to be located on the hemisphere (resulting in step 47 shown in FIG. 5), and the following steps 54–60 are included, resulting in iterative geometry reconstruction 70 of the present invention shown in FIG. 5.

In addition to the above-mentioned steps 42, 44, 46, 48, and 50 from method 40, iterative geometry reconstruction method 70 includes determining the intersection of the line through P and Q and the hemisphere (step 54). This intersection point is the new estimate of the focal spot location Q', replacing the previously determined point Q.

Next, determine new marker positions (B, B', . . . ) as the intersection of the lines through P and the respective associated projection points with the corresponding lines associated with the new focal spot position Q' (step 56).

Then, determine each remaining focal spot position (i.e., focal spots other than P and Q) as the intersection of the lines through the marker positions and their respective projections with respect to the considered focal spot position (step 58).

Subsequently, and iteratively, evaluate the relative position of the estimated focal spot positions with respect to the hemisphere. If the relative system geometry derived so far does not coincide with the absolute system geometry, then typically the majority of the reconstructed focal spot positions will not be located on the hemisphere. Choose an appropriately updated focal spot P (on the hemisphere) and go back to 48 (step 60). Repeat the foregoing iteration until all of the determined x-ray source positions are close to the hemisphere, according to a suitable criterion.

While the previously presented method 40 reconstructs a consistent geometry (which guarantees perfect image quality for the 3-dimensional image reconstruction), iterative geometry reconstruction 70 (and 54–60, particularly) results in a perfect reconstruction of the (internal) system geometry in absolute coordinates of a tomosynthesis system.

A test of the iterative geometry reconstruction method 70 of the present invention on a prototype of a tomosynthesis system 10 having a geometry as illustrated in FIG. 1 resulted in only slight deviation from the nominal system geometry (it is not known whether the nominal system geometry was also the "true" system geometry) and no discernible difference in image quality when comparing reconstructions of an imaged object using these different geometries.

The above-mentioned methods 40 and 70 are applicable to determining the tomosynthesis system geometry from projections of volumes containing markers satisfying the requirements mentioned herein above. These methods can be used to monitor mechanical system performance (deformations, repeatability of x-ray source positioning, etc.) for a tomosynthesis system and to perform a periodic recalibration of this system. In addition, using fiducial markers attached, for example, to the compression paddle (in the case of breast imaging), a recalibration of the system geometry can be performed for each single set of tomosynthesis projections, i.e., in particular when imaging patients. When using markers which are attached to the object 20 or patient (breast), the methods 40 and 70 can be used to detect patient motion and similar effects. Also, slightly modified versions of the present invention can be used to calibrate similar x-ray imaging devices, or devices that use other projection based imaging modalities (i.e., not x-ray).

A derivation of the above-mentioned tomosynthesis system geometry determination methods 40 and 70 of the present invention is presented herein below. More particularly, non-uniqueness/ambiguity in the geometry reconstruction is now discussed. The projection mapping discussed herein above relies on the family of lines passing through each of the focal spot positions (for example, P, Q) of the x-ray source 14. All points located on one of these lines are projected onto the intersection between the line and the detector plane 12. Using this interpretation of the projection geometry, every mapping of the 3-dimensional space containing the object 20, which leaves the detector plane 12 invariant, and maps lines onto lines gives rise to an alternative geometry, which is undistinguishable from the original geometry (in terms of geometric relationships within the projection images) of the tomosynthesis system. Two such "deformations" of the 3-dimensional space are:

3-dimensional-skew (shear), where each point in space is translated by a vector zh, where z denotes the height of the considered point above the detector, and h denotes an arbitrary (but fixed) horizontal vector (i.e., the z-component of h is equal to zero). A more detailed discussion of the above-mentioned skew (shear) is presented with reference to FIG. 6.

Figure 6:
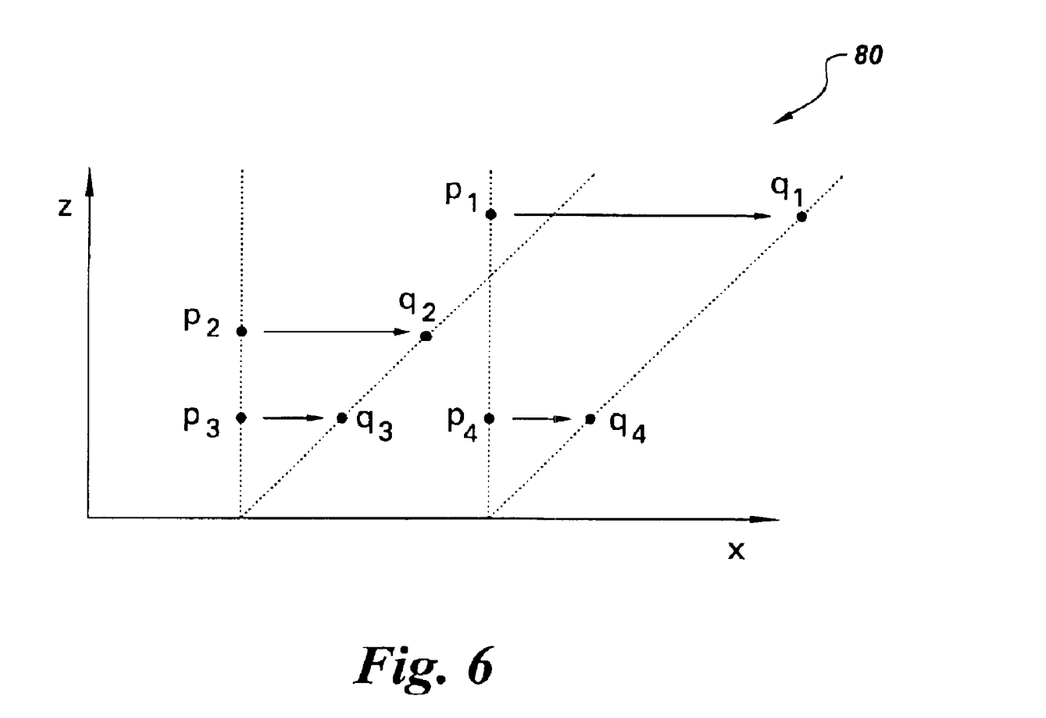
FIG. 6 illustrates the skewing (shear) of the 3-dimensional space.

Scaling in z, where the z-component of each point in space is multiplied by a fixed factor k.

FIG. 6 illustrates the "skewing" (shear) 80 of the 3-dimensional space, discussed herein above. Through skewing (or shear) 80, each point $p_i$ is mapped onto the corresponding point $q_i$. Points $p_i$ and $q_i$ are arbitrary points (and not any specific points within the tomosynthesis system geometry). If the overall tomosynthesis system geometry (this includes the geometry of the system as well as the geometry of the imaged object) is modified by such a "skewing" operation and/or the scaling in z, then the geometric relationships within the resulting projection images will remain unchanged.

A third type of ambiguity, the derivation of which relies upon Desargues' Theorem, is now discussed with reference to the geometry and notations used in FIGS. 2 and 4.

To check whether Desargues' theorem really applies to determining tomosynthesis system geometry, the marker positions B and B' are considered. For some focal spot position P, the projections C and C' of B and B', respectively, are located on a straight line which is given by the intersection of:

the detector plane 12 with a plane containing P, B, and B' (not shown in FIGS. 2 and 4).

Varying now the focal spot position P, a family of planes (spanned by B, B', and the considered focal spot P) is obtained, all containing the line through B and B', as discussed herein above. This family of planes in turn defines a family of straight lines in the detector plane 12. All of these lines intersect at a common point, which is exactly the point O where the line through B,B' intersects the detector plane 12. Therefore the assumptions of Desargues' theorem are satisfied.

The points A, C and A', C' are the shadows of the (unknown) markers B, B', with respect to the (unknown) focal spot positions P and Q. These observed points do, however, uniquely define the points O and S. Only in the case when P and Q have the same height above the detector, S is not uniquely defined.

As in the above-mentioned methods 40 (process 46) and 70 (processes 47 or 60), first an arbitrary focal spot position P is selected, and then either Q as some arbitrary point on the line through the points P and S, or B on the line through P and C (where B is to be located between P and C), or B' on the line through P and C' (where B' is to be located between P and C')

is chosen.

Through any one of these choices, the points Q, B and B' are completely defined (since the line through B, B' intersects the detector plane 12 in the point O, and A, B, Q as well as A', B', Q, respectively, are located on a straight line).

Assuming that the chosen location P is the true location of the corresponding focal spot position, then some arbitrary Q located on the line through P and S is selected, which generates the above-mentioned ambiguity of the third kind.

Using the already reconstructed elements (i.e., the location of the points A, A', C, C', B, B', P and Q), the locations of additional markers and focal spot positions are then determined.

The recovered geometry is now demonstrated to be consistent, in particular, when more than two fiducial markers and more than two focal spot positions are considered.

Note here that an additional marker B", seen in conjunction with any one of the already considered markers B or B', exhibits the corresponding geometric properties as the pair of markers (B,B'). In particular, any considered pair of markers has an associated point (the point corresponding to O), where the logical line through both markers intersects the detector plane. For any given focal spot location, the line through the corresponding projections of the two markers also goes through this point. Furthermore, any additional focal spot position R, seen in conjunction with any one of the already considered focal spot positions P or Q, exhibits the corresponding geometric properties as the pair of focal spot positions (P,Q). In particular, any considered pair of focal spot positions has an associated point (the point corresponding to S), where the logical line through both focal spot positions intersects the detector plane. For any given marker, the line through the projections of this marker with respect to the considered focal spot positions goes also through this point.

If additional markers are added to the imaged volume of tomosynthesis system 10, define B" (not shown in FIG. 3, but consistent with the foregoing discussion with reference to marker B') as the intersection of the lines joining the focal spot positions P and Q with the respective projections C" and A" (not shown in FIG. 3, but consistent with the foregoing discussion with reference to projections C' and A'). The point B" is well-defined, i.e., these lines do indeed intersect (this can easily be seen by noting that A", C" and S lie on a straight line, and therefore A", C", P and Q lie on a plane). Furthermore B" is consistent with the previously determined geometry of the tomosynthesis system 10. In particular, an immediate result of the (dual) Desargues' theorem is that the lines through B, B" (and B', B") intersect with the detector plane 12 at the correct location O' (or O"), which proves the consistency of the recovered geometry of the tomosynthesis system. The same argument applies to other additional markers as well.

Further, the new focal spot location R is now added to the previously determined geometry of the tomosynthesis system. In particular, the focal spot P is first considered together with the new (and unknown) focal spot position R. As discussed herein above, all marker positions (B, B', B", . . . ) are in consistent locations. Thus, the line through any arbitrarily chosen pair of markers intersects the lines through the corresponding projections (with respect to P, and R, respectively) at the correct location (which is, for example, the point O if the pair B, B' of markers was chosen). Therefore Desargues' theorem applies again, and, hence, P, R, and S' (which is uniquely determined from the projection data) lie on a straight line. In particular, R is determined alternatively:

either as the intersection of a line through any single marker and its corresponding projection (with respect to R) with the line through P and S', or as the intersection of the lines through the marker positions and their respective projections (again with respect to R).

The first alternative indicated above is furthermore used to show that now the reconstructed geometry of the tomosynthesis system is fully consistent. In a similar manner, other, additional focal spot positions can be introduced, and the resulting overall geometry remains consistent.

Determination of the tomosynthesis system geometry in the present invention does not depend upon the use of a specific phantom with precisely defined locations of fiducial markers. Thus, the present invention is flexible by allowing the use of different phantoms as well as employing low-cost phantoms (where the location of markers may only be roughly specified) for tomosynthesis system geometry calibration. Moreover, when used in conjunction with several single markers which remain in the imaged volume during clinical imaging procedures, the present invention allows for system geometry reconstruction, and thus perfect image quality even if, for example, the focal spot positions drift over time.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A method of determining geometry of a tomosynthesis system including a detector and an x-ray source, said method comprising the steps of:

arbitrarily identifying at least two markers within an imaged volume, the at least two markers being placed at different relative distances between the detector and the x-ray source, and without having projections located on a straight line for all different source positions; and locating the projections of the markers within at least two images acquired of the imaged volume, said at least two images corresponding to different positions of a focal spot of the x-ray source wherein said step of locating is performed using a computer of the tomosynthesis system.

2. The method as in claim 1, wherein the step of locating determines the focal spot positions of the x-ray source relative to the detector.

3. The method as in claim 1, wherein the step of locating determines the relative geometry of the tomosynthesis system.

4. The method as in claim 1, wherein the step of locating determines absolute tomosynthesis system geometry with respect to a fixed coordinate system within the tomosynthesis system.

5. The method as in claim 1, wherein the markers comprise anatomical markers.

6. The method as in claim 1, wherein the projections of the markers are located manually.

7. The method as in claim 1, further comprising the step of:

reconstructing the geometry based upon the step of locating, said reconstructing comprising the steps of:

identifying the detector coordinates of projections of the markers onto the detector for each projection image and for each projection of a marker;

identifying an index of the corresponding marker and an index of a corresponding focal spot position of the x-ray source for each projection image and for each projection of a marker;

determining for at least one pair of markers the intersection of the line through the projections of the markers with respect to at least an unknown first focal spot position with the line through the projections of the markers with respect to at least an unknown second focal spot position, said point of intersection being identical to the point of intersection of the line drawn through the pair of markers with the plane comprising the detector;

arbitrarily selecting a first focal spot position of the x-ray source;

selecting a first one of the marker positions relative to the first source position and the position of the corresponding projection of the one marker;

determining a second one of the marker positions relative to (1) the first one of the marker positions, (2) the first source position, (3) the position of the corresponding projection of the second marker, and (4) the point of intersection of the line drawn through the pair of markers with the plane comprising the detector; and determining a second source position relative to (1) the first one of the marker positions, (2) the second one of the marker positions, and (3) the respective positions of the projections of the two markers with respect to the second source position.

8. The method as in claim 7, wherein the first x-ray source position is selected arbitrarily on a hemisphere determined by the length of a gantry arm supporting the x-ray source and a location of the pivot point of the gantry arm, said method further comprising the steps of:

modifying the second x-ray source position such that the second x-ray source position is located on the hemisphere, by drawing a line through the first and the second focal spot position and by determining a point of the intersection of that line with the hemisphere, wherein the point of intersection determines the modified second x-ray source position, re-determining the first one of the marker positions and the second one of the marker positions based upon the first x-ray source position and the modified, second x-ray source position, and the respective positions of the corresponding projections of the two markers, determining additional x-ray source positions based upon the re-determined first one of the marker positions and the re-determined second one of the marker positions, and the respective positions of the corresponding projections of the two markers, evaluating relative positions of additional x-ray source positions with respect to the hemisphere, and updating the first x-ray source position according to the evaluating, and iteratively executing the modifying, the re-determining, the determining additional source positions, and evaluating until all of the determined x-ray source positions are close to the hemisphere.

9. The method as in claim 1, wherein the focal spot positions vary between acquisitions of a set of projection radiographs of the imaged volume and are periodically determined.

10. The method as in claim 1, wherein the focal spot positions vary with each acquisition of a set of projection radiographs of the imaged volume and are determined subsequent to each acquisition of a set of projection radiographs of the imaged volume.

11. The method as in claim 1, where the markers are attached to the imaged object, and the projections of the markers are used by the tomosynthesis system to detect movement of the object during the image acquisition process.

12. The method as in claim 1, wherein the object is a patient.

13. The method as in claim 1, wherein the markers are provided in a phantom comprising a non-rigid structure.

14. A tomosynthesis system for imaging an object, the tomosynthesis system comprising:

an x-ray source for emitting x-rays, the x-ray source having different focal spot positions as said x-ray source moves relative to the object;

a detector positioned relative to the x-ray source for receiving the emitted x-rays as the x-ray source moves relative to the object; and a computer coupled to the x-ray source and the detector, the computer executing processes determining a geometry of the tomosynthesis system, wherein at least two markers are identified arbitrarily within an imaged volume of the object, at different relative distances between the detector and the x-ray source, and without having projections located on a straight line for all different x-ray source positions, and wherein said computer executes processes locating the projections of the markers within at least two images acquired from the imaged volume, said at least two images corresponding to the different positions of the focal spot of the x-ray source.

15. The tomosynthesis system as in claim 14, wherein the computer determines the focal spot positions of the x-ray source relative to the detector.

16. The tomosynthesis system as in claim 14, wherein the computer determines the relative geometry of the tomosynthesis system.

17. The tomosynthesis system as in claim 14, wherein the markers comprise anatomical markers.

18. The tomosynthesis system as in claim 14, wherein the projections of the markers are located manually.

19. The tomosynthesis system as in claim 14, wherein the locating determines an absolute tomosynthesis system geometry with respect to a fixed coordinate system within the tomosynthesis system.

20. The tomosynthesis system as in claim 14, wherein said computer executes processes further comprising the steps of:

reconstructing the geometry based upon the locating of the projections of the markers, said reconstructing comprising the steps of:

identifying the detector coordinates of projections of the markers onto the detector for each projection image and for each projection of a marker;

identifying an index of the corresponding marker and an index of a corresponding focal spot position of the x-ray source for each projection image and for each projection of a marker;

determining for at least one pair of markers the intersection of the line through the projections of the markers with respect to an unknown first focal spot position with the line through the projections of the markers with respect to an unknown second focal spot position, said point of intersection being identical to the point of intersection of the line drawn logically through the pair of markers with the plane comprising the detector;

arbitrarily selecting a first focal spot position of the x-ray source;

selecting a first one of the marker positions relative to the first source position and the position of the corresponding projection of the one marker;

determining a second one of the marker positions relative to (1) the first one of the marker positions, (2) the first source position, (3) the position of the corresponding projection of the second marker, and (4) the point of intersection of the line drawn through the pair of markers with the plane comprising the detector; and determining a second source position relative to (1) the first one of the marker positions, (2) the second one of the marker positions, and (3) the respective positions of the projections of the two markers with respect to the second source position.

21. The tomosynthesis system as in claim 20, wherein the computer executes processes further comprising the steps of:

selecting the first x-ray source position arbitrarily on a hemisphere determined by the length of a gantry arm supporting the x-ray source and a location of the pivot point of the gantry arm;

modifying the second x-ray source position such that the second x-ray source position is located on the hemisphere, by drawing a line through the first and the second focal spot position and by determining a point of the intersection of that line with the hemisphere, wherein the point of intersection determines the modified second x-ray source position;

re-determining the first one of the marker positions and the second one of the marker positions based upon the first x-ray source position and the modified, second x-ray source position and the respective positions of the corresponding projections of the two markers;

determining additional x-ray source positions based upon the re-determined first one of the marker positions and the re-determined second one of the marker positions, and the respective positions of the corresponding projections of the two markers;

evaluating relative positions of additional x-ray source positions with respect to the hemisphere; and updating the first x-ray source position according to the steps of evaluating, and iteratively executing the modifying, the re-determining, the determining additional source positions, and evaluating until all of the determined x-ray source positions are close to the hemisphere.

22. The tomosynthesis system as in claim 14, wherein the focal spot positions vary between acquisitions of a set of projection radiographs of the imaged volume and are periodically determined.

23. The tomosynthesis system as in claim 14, wherein the focal spot positions vary with each acquisition of a set of projection radiographs of the imaged volume and are determined subsequent to each acquisition of a set of projection radiographs of the imaged volume.

24. The tomosynthesis system as in claim 14, where the markers are attached to the imaged object, and the projections of the markers are used by the computer of the tomosynthesis system to detect movement of the object during the image acquisition process.

25. The tomosynthesis system as in claim 14, wherein the object is a patient.

26. The tomosynthesis system as in claim 14, wherein the markers are provided in a phantom comprising a non-rigid structure.

27. A computer-readable medium storing a program determining geometry of a tomosynthesis system including a detector, an x-ray source and at least two markers arbitrarily identified within an imaged volume, at different relative distances between the detector and the x-ray source, and without having projections located on a straight line for all different source positions, said program which when executed by a computer causes the computer to execute the processes comprising the steps of:

locating the projections of the markers within at least two images acquired of the imaged volume using the computer of the tomosynthesis system, said at least two images corresponding to different positions of a focal spot of the x-ray source.

28. The computer-readable medium as in claim 27, wherein the locating determines the focal spot positions of the x-ray source relative to the detector.

29. The computer-readable medium as in claim 27, wherein the locating determines the relative geometry of the tomosynthesis system.

30. The computer-readable medium as in claim 27, wherein the locating determines absolute tomosynthesis system geometry with respect to a fixed coordinate system within the tomosynthesis system.

31. The computer-readable medium as in claim 27, wherein the program executed by the computer causes the computer to execute the processes further comprises the steps of:

reconstructing the geometry based upon the locating, said reconstructing comprising the steps of:

identifying the detector coordinates of projections of the markers onto the detector for each projection image and for each projection of a marker;

identifying an index of the corresponding marker and an index of a corresponding focal spot position of the x-ray source for each projection image and for each projection of a marker;

determining for at least one pair of markers the intersection of the line through the projections of the markers with respect to an unknown first focal spot position with the line through the projections of the markers with respect to an unknown second focal spot position, said point of intersection being identical to the point of intersection of the line drawn through the pair of markers with the plane comprising the detector;

arbitrarily selecting a first focal spot position of the x-ray source;

selecting a first one of the marker positions relative to the first source position and the position of the corresponding projection of the one marker;

determining a second one of the marker positions relative to (1) the first one of the marker positions, (2) the first source position, (3) the position of the corresponding projection of the second marker, and (4) the point of intersection of the line drawn through the pair of markers with the plane comprising the detector; and determining a second source position relative to (1) the first one of the marker positions, (2) the second one of the marker positions, and (3) the respective positions of the projections of the two markers with respect to the second source position.

32. The computer-readable medium as in claim 31, wherein the first x-ray source position is selected arbitrarily on a hemisphere determined by the length of a gantry arm supporting the x-ray source and a location of the pivot point of the gantry arm, said wherein the program executed by the computer causes the computer to execute the processes further comprises the steps of:

modifying the second x-ray source position such that the second x-ray source position is located on the hemisphere, by drawing a line through the first and the second focal spot position and by determining a point of the intersection of that line with the hemisphere, wherein the point of intersection determines the modified second x-ray source position, re-determining the first one of the marker positions and the second one of the marker positions based upon the first x-ray source position and the modified, second x-ray source position, and the respective positions of the corresponding projections of the two markers, determining additional x-ray source positions based upon the re-determined first one of the marker positions and the re-determined second one of the marker positions, and the respective positions of the corresponding projections of the two markers, evaluating relative positions of additional x-ray source positions with respect to the hemisphere, and updating the first x-ray source position according to the evaluating, and iteratively executing the modifying, the re-determining, the determining additional source positions, and evaluating until all of the determined x-ray source positions are close to the hemisphere.

33. The computer-readable medium as in claim 27, wherein the focal spot positions vary with each acquisition of the imaged volume and are determined subsequent to each acquisition of the imaged volume.

34. The computer-readable medium as in claim 27, where the markers are attached to the imaged object, and the projections of the markers are used by the tomosynthesis system to detect movement of the object during the image acquisition process.

35. The computer-readable medium as in claim 27, wherein the object is a patient.

36. The computer-readable medium as in claim 27, wherein the markers are provided in a phantom comprising a non-rigid structure.

37. The computer-readable medium as in claim 27, wherein the markers are provided in a phantom comprising a non-rigid structure.

38. A method of determining geometry of a tomosynthesis system including a detector and an x-ray source, said method comprising the steps of:
- locating projections of markers wherein the markers are identified at different relative distances between the detector and the x-ray source;
- drawing logic lines through pairs of locations of projections;
- determining points of intersection of these lines in the detector plane; and
- determining points in three-dimensional space, wherein the logic lines drawn through the pairs of points intersect a detector plane at predetermined points in the detector plane.

39. A tomosynthesis system for imaging an object, the tomosynthesis system comprising:
- an x-ray source for emitting x-rays, the x-ray source having different focal spot positions as said x-ray source moves relative to the object;
- a detector positioned relative to the x-ray source for receiving the emitted x-rays as the x-ray source moves relative to the object; and
- a computer coupled to the x-ray source and the detector, the computer executing processes determining a geometry of the tomosynthesis system, wherein projections of markers are located and the markers are identified at different relative distances between the detector and the x-ray source, logic lines are drawn through pairs of locations of projections, and points of intersection of these lines in the detector plane are determined, and points in three-dimensional space are determined, and wherein logic lines drawn through pairs of said points intersect a detector plane at predetermined points in the detector plane.

* * * * *